US012138199B2

(12) United States Patent
Tal et al.

(10) Patent No.: US 12,138,199 B2
(45) Date of Patent: *Nov. 12, 2024

(54) INTRAUTERINE DEVICE WITH RETRIEVAL THREAD (71) Applicant: SEBELA VLC LIMITED, Hamilton (BM)

(72) Inventors: Michael Tal, Savyon (IL); Bob H. Katz, San Jose, CA (US); Mark James DeBisschop, Harwinton, CT (US)

(73) Assignee: Sebela VLC Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,253

(22) Filed: Jul. 24, 2023

(65) Prior Publication Data

US 2024/0139024 A1 May 2, 2024

Related U.S. Application Data

(60) Continuation of application No. 17/456,275, filed on Nov. 23, 2021, now Pat. No. 11,744,728, which is a
(Continued)

(51) Int. Cl.
*A61F 6/18* (2006.01)
*A61F 6/06* (2006.01)
(Continued)

(52) U.S. Cl.
CPC ................ *A61F 6/18* (2013.01); *A61F 6/06* (2013.01); *A61F 6/14* (2013.01); *A61F 6/142* (2013.01); *A61F 6/144* (2013.01); *A61K 9/0039* (2013.01)

(58) Field of Classification Search
CPC ..... A61K 9/0039; A61K 9/0036; A61F 6/142; A61F 6/144; A61F 6/18; A61F 6/14;
(Continued)

(56) References Cited

U.S. PATENT DOCUMENTS

| 662,716 A | 11/1900 | Gaedeke |
| 3,407,806 A | 10/1968 | Hulka et al. |
| (Continued) | | |

FOREIGN PATENT DOCUMENTS

| CN | 2231089 Y | 7/1996 |
| CN | 202096333 U | 1/2012 |
| (Continued) | | |

OTHER PUBLICATIONS

Extended European Search Report for Application No. 14853624.6, dated Mar. 17, 2017, 7 pages.
(Continued)

*Primary Examiner* — Tarla R Patel
(74) *Attorney, Agent, or Firm* — Giordano Law LLC; David A. Giordano (57) ABSTRACT

An intrauterine contraceptive system may include a contraceptive intrauterine device, a retrieval thread permanently attached to the intrauterine device and an insertion device for inserting the intrauterine device into a uterus. The system may also include a release thread releasably coupled with the intrauterine device. The intrauterine device may be deployable out of a distal end of the insertion device and may be configured to change from a delivery configuration when housed in the insertion device to a deployed configuration when deployed in a uterus. The retrieval thread and the optional release thread may be at least partially housed within the insertion device during insertion of the intrauterine device into the uterus. The release thread may extend from the intrauterine device through the insertion device to an attachment point at or near a proximal end of the insertion device.

11 Claims, 7 Drawing Sheets

Related U.S. Application Data continuation of application No. 16/552,825, filed on Aug. 27, 2019, now Pat. No. 11,207,209, which is a continuation of application No. 15/477,189, filed on Apr. 3, 2017, now Pat. No. 10,398,588, which is a continuation of application No. 14/794,274, filed on Jul. 8, 2015, now Pat. No. 9,610,191, which is a division of application No. 14/057,297, filed on Oct. 18, 2013, now Pat. No. 9,180,040.

(51) Int. Cl.
*A61F 6/14* (2006.01)
*A61K 9/00* (2006.01)

(58) Field of Classification Search
CPC ......... A61F 6/146; A61F 6/20; A61M 31/002; A61M 29/00; A61B 17/12022; A61B 17/0057
USPC ....................................................... 128/833
See application file for complete search history.

(56) References Cited

U.S. PATENT DOCUMENTS

| | | | |
|---|---|---|---|
| 3,492,990 | A | 2/1970 | Clarke |
| 3,678,927 | A | 7/1972 | Soichet |
| 3,750,662 | A | 8/1973 | Lerner |
| 3,789,838 | A | 2/1974 | Fournier et al. |
| 3,902,483 | A | 9/1975 | Place et al. |
| 3,911,911 | A | 10/1975 | Scommegna |
| 3,973,560 | A | 8/1976 | Emmett |
| 3,996,933 | A | 12/1976 | Gutnick |
| 4,136,695 | A | 1/1979 | Dafoe |
| 4,416,660 | A | 11/1983 | Dafoe |
| 4,762,130 | A | 8/1988 | Fogarty et al. |
| 5,303,719 | A | 4/1994 | Wilk |
| 5,507,725 | A | 4/1996 | Savage et al. |
| RE35,636 | E | 10/1997 | Diaz et al. |
| 5,785,053 | A | 7/1998 | Macandrew et al. |
| 6,119,696 | A | 9/2000 | Turin |
| 6,152,943 | A | 11/2000 | Sawhney |
| 6,588,429 | B1 | 7/2003 | Wildemeersch |
| 6,682,526 | B1 | 1/2004 | Jones |
| 6,709,667 | B1 | 3/2004 | Lowe et al. |
| 6,742,520 | B1 | 6/2004 | Wildemeersch |
| 7,506,650 | B2 | 3/2009 | Lowe et al. |
| 7,591,268 | B2 | 9/2009 | Lowe et al. |
| 7,621,276 | B2 | 11/2009 | Tal et al. |
| 7,661,429 | B2 | 2/2010 | Jutila |
| 7,669,601 | B2 | 3/2010 | Tal |
| 8,011,370 | B2 | 9/2011 | Karabey |
| 8,079,364 | B2 | 12/2011 | Lowe et al. |
| 8,181,653 | B2 | 5/2012 | Tal et al. |
| 8,435,205 | B2 | 8/2013 | Arora et al. |
| 8,573,222 | B2 | 11/2013 | Weintraub |
| 8,662,081 | B2 | 3/2014 | Tal et al. |
| 8,700,120 | B2 | 4/2014 | Koblish |
| 9,016,280 | B2 | 4/2015 | Tal et al. |
| 9,089,418 | B2 | 7/2015 | Tal et al. |
| 9,180,039 | B2 | 11/2015 | Tal et al. |
| 9,180,040 | B2 * | 11/2015 | Tal ............................ A61F 6/142 |
| 9,265,652 | B2 | 2/2016 | Tal et al. |
| 9,427,351 | B2 | 8/2016 | Tal et al. |
| 9,492,311 | B2 | 11/2016 | Tal et al. |
| 9,510,088 | B2 | 11/2016 | Tal et al. |
| 9,610,191 | B2 | 4/2017 | Tal et al. |
| 10,022,264 | B2 * | 7/2018 | Tal ............................ A61F 6/06 |
| 10,398,588 | B2 * | 9/2019 | Tal ............................ A61F 6/144 |
| 11,207,209 | B2 * | 12/2021 | Tal ............................ A61F 6/06 |
| 2004/0163651 | A1 | 8/2004 | Nikolchev et al. |
| 2005/0187561 | A1 | 8/2005 | Lee-Sepsick et al. |
| 2005/0240211 | A1 | 10/2005 | Sporri et al. |
| 2005/0274384 | A1 | 12/2005 | Tran et al. |
| 2008/0047563 | A1 | 2/2008 | Tal et al. |
| 2008/0135053 | A1 | 6/2008 | Gruber et al. |
| 2008/0216842 | A1 | 9/2008 | Acedo |
| 2010/0300452 | A1 | 12/2010 | Tal et al. |
| 2011/0061659 | A1 | 3/2011 | Cruzada et al. |
| 2011/0162656 | A1 | 7/2011 | Jutila et al. |
| 2011/0166508 | A1 | 7/2011 | Lyytikinen et al. |
| 2011/0172593 | A1 | 7/2011 | Lyyikinen et al. |
| 2012/0097172 | A1 | 4/2012 | Tal et al. |
| 2012/0111338 | A1 | 5/2012 | Weitraub |
| 2012/0130410 | A1 | 5/2012 | Tal et al. |
| 2013/0014762 | A1 | 1/2013 | Deckman et al. |
| 2013/0019374 | A1 | 1/2013 | Schwartz |
| 2013/0068234 | A1 | 3/2013 | Pandit |
| 2013/0152942 | A1 | 6/2013 | Lyytikinen et al. |
| 2013/0211321 | A1 | 8/2013 | Dubois et al. |
| 2013/0213406 | A1 | 8/2013 | Frankenne et al. |
| 2013/0217960 | A1 | 8/2013 | Arora et al. |
| 2013/0220338 | A1 | 8/2013 | Lyyikainen et al. |
| 2013/0255695 | A1 | 10/2013 | Jutila et al. |
| 2013/0312761 | A1 | 11/2013 | Wijay |
| 2013/0319424 | A1 | 12/2013 | Weintraub |
| 2014/0041667 | A1 | 2/2014 | Cammack |
| 2014/0048073 | A1 | 2/2014 | Tal et al. |
| 2014/0048074 | A1 | 2/2014 | Tal et al. |
| 2014/0076328 | A1 | 3/2014 | Lyytikainen et al. |
| 2015/0025310 | A1 | 1/2015 | Everinghman |
| 2015/0101613 | A1 | 4/2015 | Tal et al. |
| 2015/0313753 | A1 | 11/2015 | Tal et al. |
| 2015/0335465 | A1 | 11/2015 | Tal et al. |
| 2016/0058608 | A1 | 3/2016 | Tal et al. |
| 2016/0331579 | A1 | 11/2016 | Tal et al. |
| 2017/0056237 | A1 | 3/2017 | Tal et al. |
| 2017/0165103 | A1 | 6/2017 | Tal et al. |

FOREIGN PATENT DOCUMENTS

| | | |
|---|---|---|
| CN | 203138640 U | 8/2013 |
| CN | 203970514 U | 12/2014 |
| EP | 2 327 381 A1 | 6/2011 |
| WO | 80/00536 A1 | 4/1980 |
| WO | 90/09158 A1 | 8/1990 |
| WO | 2007/136965 A1 | 11/2007 |
| WO | 2008/048764 A1 | 4/2008 |
| WO | 2010/036721 A1 | 4/2010 |
| WO | 2012/027090 A1 | 3/2012 |
| WO | 2014/028499 A2 | 2/2014 |

OTHER PUBLICATIONS

International Search Report and Written Opinion for Application No. PCT/US2014/056967, mailed Jan. 9, 2015, 7 pages.

* cited by examiner

INTRAUTERINE DEVICE WITH RETRIEVAL THREAD

CROSS-REFERENCE TO RELATED APPLICATIONS

This application is a continuation application of U.S. patent application Ser. No. 17/456,275, filed Nov. 23, 2021, and issued on Sep. 5, 2023 as U.S. Pat. No. 11,744,728, which is a continuation application of U.S. patent application Ser. No. 16/552,825, filed Aug. 27, 2019, and issued on Dec. 28, 2021 as U.S. Pat. No. 11,207,209, which is a continuation application of U.S. patent application Ser. No. 15/477,189, filed Apr. 3, 2017, and issued on Sep. 3, 2019, as U.S. Pat. No. 10,398,588, which is a continuation application of U.S. patent application Ser. No. 14/794,274, filed Jul. 8, 2015, and issued on Apr. 4, 2017, as U.S. Pat. No. 9,610,191, which is a divisional application of U.S. patent application Ser. No. 14/057,297, filed Oct. 18, 2013, and issued on Nov. 10, 2015, as U.S. Pat. No. 9,180,040. The disclosures of the above referenced patent applications are hereby fully incorporated by reference.

FIELD OF THE INVENTION

The present invention relates to medical devices. More specifically, the invention relates to intrauterine devices for contraception.

BACKGROUND

An intrauterine device (IUD) is a small, often T-shaped device, containing copper or hormone (e.g., Levonorgestrel), which is inserted into the uterus to provide long-acting, reversible contraception. Intrauterine devices are the most widely used form of reversible contraception, with more than 180 million users worldwide.

Copper IUDs primarily work by disrupting sperm mobility and damaging sperm so that the sperm are prevented from joining with an egg. Copper acts as a spermicide within the uterus, increasing levels of copper ions, prostaglandins, and white blood cells within the uterine and tubal fluids. The increased copper ions in the cervical mucus inhibit the sperm's motility and viability, preventing sperm from traveling through the cervical mucus or destroying it as it passes through. Copper IUDs have a first-year pregnancy-prevention success rate ranging from 97.8 to 99.9 percent. The Paragard® intrauterine copper contraceptive device (www-.paragard.com) is currently the most common copper IUD. Copper IUDs can typically be implanted for up to 10 years.

Advantages of the copper IUD include its ability to provide emergency contraception up to five days after unprotected sex. It is generally known as the most effective form of emergency contraception available. It contains no hormones, so it can be used while breast feeding, and fertility returns quickly after removal. Copper IUDs are also available in a wider range of sizes and shapes than hormonal IUDs. Disadvantages include the possibility of heavier menstrual periods and more painful menstrual cramping.

A hormonal IUD, such as the Mirena® levonorgestrel-releasing intrauterine system (www.mirena-us.com), uses the controlled release of a hormonal contraceptive such as levonorgestrel (a progestin). The hormonal contraceptive released from a hormonal IUD prevents ovulation from occurring, so an egg is never released. The hormone also thickens the cervical mucus so that sperm cannot reach the fallopian tubes. Hormonal IUDs can be implanted for up to 5 years.

Hormonal IUDs do not increase bleeding as copper-containing IUDs do. Instead, they can often reduce menstrual bleeding or prevent menstruation altogether, and thus they are sometimes used as a treatment for menorrhagia (heavy menstrual bleeding). Hormonal IUDs do have common side effects, however. The most common side effects with levonorgestrel IUDs are hormone-related effects, such as headaches, nausea, breast tenderness, depression and cyst formation.

Regardless of the contraceptive mechanism, IUDs almost always include one or two threads, which are attached at the distal (cervical) end of the IUD, and which have two uses. First, the IUD thread is used to remove the IUD when desired, by the physician pulling on the thread to dislodge the IUD from the uterus and pull it through the cervix and out the vaginal cavity. For this purpose, the thread must be long enough to traverse the cervical canal and extend into the vaginal cavity. Second, the thread is used to confirm that the IUD is still in place. This is done either by the physician on vaginal exam or by the women herself feeling the thread with her finger. Third, the thread is currently used to load the IUD into the IUD insertion device and secure it within the inserter during advancement of the distal end of the inserter into the uterus. Because the thread is used for loading and securing the IUD in the inserter, it must be long enough to extend through the inserter to its proximal end. This means that the thread must be much longer than it would need to be if used only for IUD retrieval or verification. Thus, currently available IUD systems require the physician to insert sterile, sharp scissors or another cutting instrument into the vaginal cavity after IUD placement and cut the extra-long thread to a useful length for later IUD retrieval. It is not practical to leave the IUD thread uncut, because it would extend out of the vagina, causing physical discomfort to the user, discomfort during sexual intercourse, significant risk of infection, and significant risk of accidental removal of the IUD by pulling on the dangling thread.

Therefore, after an IUD is delivered into the uterus, the IUD insertion device is removed from the body, leaving the IUD in the uterus and the long thread extending through the cervix into the vaginal cavity. The physician must then insert sterile scissors into the vaginal cavity to cut the thread to a shorter length, so that the thread still extends into the vaginal cavity but does not extend too far into or out of the vaginal cavity. The remaining end portion of the thread then typically wraps around the cervical fornix.

Although currently available IUD threads work for their intended purpose, inserting the IUD requires additional time and the additional step of trimming the thread. This step involves inserting scissors or some other sharp cutting device into the vaginal cavity, which adds time and potential discomfort to an IUD insertion procedure and increases the risk of accidentally dislodging the IUD from the uterus. In a worst case scenario, the thread cutting step may even cause injury and/or infection to the patient, due to the required insertion and manipulation of a sharp cutting device in the vaginal cavity. Therefore, it would be advantageous to have an IUD device with an improved thread or other retrieval mechanism that did not require trimming or other, additional steps during an IUD insertion procedure.

BRIEF SUMMARY

Disclosed herein are various embodiments of an improved IUD and IUD insertion system. Generally, the described embodiments allow an IUD to be safely and reliably delivered into a uterus without requiring the additional step of cutting a thread attached to the IUD.

In one aspect, an intrauterine contraceptive system may include a contraceptive intrauterine device, a retrieval thread permanently attached to the intrauterine device and having a length of between about 5 centimeters and about 9 centimeters, and an insertion device for inserting the intrauterine device into a uterus. The intrauterine device may be deployable out of a distal end of the insertion device and may be configured to change from a delivery configuration when housed in the insertion device to a deployed configuration when deployed in a uterus. The retrieval thread may be at least partially housed within the insertion device during insertion of the intrauterine device into the uterus.

In some embodiments, the system may also include a release thread releasably coupled with the intrauterine device. The release thread may extend from the intrauterine device through the insertion device to an attachment point at or near a proximal end of the insertion device. In some embodiments, the intrauterine device may include an opening, the retrieval thread may be attached to the intrauterine device at or near the opening, and the release thread may pass through the opening. In some embodiments, the release thread may have a length sufficient to allow it to pass from the attachment point through the intrauterine device and back to the attachment point.

Optionally, the retrieval thread may include a first portion having a first color and a second portion having a second color, where the first and second colors contrast with one another sufficiently to be visible during a physical examination of a patient in which the intrauterine device has been placed. In some embodiments, the first portion may extend from a point of attachment of the retrieval thread with the intrauterine device to a location along the retrieval thread between about 2 centimeters and about 3 centimeters from the point of attachment. In some embodiments, the retrieval thread may include a third portion having the first color, where the second portion is a band of the second color, with the first and third portions on either side of the band.

In another aspect, an intrauterine contraceptive device may include a frame and a retrieval thread permanently attached to the frame and having a length of between about 5 centimeters and about 9 centimeters. Optionally, the frame may include an opening, and the retrieval thread may be attached to the frame at or near the opening. Some embodiments of the device may also include a release thread releasably coupled with the frame for coupling the intrauterine device with an insertion device. In some embodiments, the retrieval thread may include a first portion having a first color and a second portion having a second color, where the first and second colors contrast with one another sufficiently to be visible during a physical examination of a patient in which the intrauterine device has been placed. For example, the first portion may extend from a point of attachment of the retrieval thread with the frame to a location along the retrieval thread between about 2 centimeters and about 3 centimeters from the point of attachment. Optionally, the retrieval thread may include a third portion having the first color, where the second portion comprises a band of the second color, with the first and third portions on either side of the band.

In another aspect, a method for delivering a contraceptive intrauterine device into a uterus may involve: advancing a distal end of an insertion device through a vaginal cavity and a cervix and into the uterus; advancing the intrauterine device out of the distal end of the insertion device, into the uterus, where the intrauterine device is permanently attached to a retrieval thread and removably coupled with a release thread; pulling the release thread off of the intrauterine device; and removing the release thread and the insertion device from the uterus, leaving the intrauterine device behind in the uterus, without cutting the retrieval thread. After delivery of the IUD into the uterus, the retrieval thread extends from an attachment point of the retrieval thread with the intrauterine device through the cervix into the vaginal cavity.

In some embodiments, the method may further involve controlling advancement of the intrauterine device out of the distal end of the insertion device, using the release thread. In some embodiments, the method may also involve manipulating the intrauterine device during or after advancing it out of the distal end of the insertion device, by manipulating the release thread. Optionally, pulling the release thread may involve pulling one end of the release thread, and wherein the release thread is looped through the intrauterine device. In some embodiments, removing the release thread and the insertion device from the uterus may involve removing the release thread first, by pulling it out through the insertion device, and after removing the release thread, pulling the insertion device out of the uterus. Alternatively, removing the release thread and the insertion device from the uterus may involve pulling the release thread and the insertion device out of the uterus together, at the same time.

The method may also optionally involve viewing the retrieval thread in the vaginal cavity after removing the release thread and the insertion device from the uterus. For example, the method may include confirming delivery of the intrauterine device sufficiently far into the uterus to perform contraception, based on viewing the retrieval thread. Viewing the retrieval thread may involve, for example, viewing a colored marker on the thread, where the marker is located a known distance from the attachment point of the retrieval thread with the intrauterine device. Alternatively, viewing the retrieval thread may involve viewing a color change at a point along the thread, where the point is located a known distance from the attachment point of the retrieval thread with the intrauterine device.

These and other aspects and embodiments will be described in further detail below, in reference to the attached drawing figures.

DETAILED DESCRIPTION

Current IUDs typically include a long, two-string thread, attached to the distal end of the IUD, extending through the inner sheath of the IUD inserter, and secured at the proximal end of the inserter. This long thread is used to first load the IUD into the distal end of the inserter system for delivery, then to hold the IUD securely in place at the distal tip of the inserter until it is placed and released in the uterine space. After IUD delivery in the uterus, the long thread is released from the inserter proximal end, and the inserter is withdrawn over the long thread. The clinician must then cut the long thread to a length, typically 3 to 4 cm beyond the external cervical os (the opening of the cervix facing into the vaginal cavity). As discussed above, this thread cutting step takes time, requires additional sterile instrumentation, is uncomfortable for the patient, and involves inherent risks of dislodging the IUD and even injury and infection, as the clinician must insert a sharp cutting device into the vaginal cavity to cut the thread.

The embodiments disclosed in this application provide for an IUD with a retrieval thread having a predetermined length that does not require cutting after delivery of the IUD into the uterus. Also disclosed herein is a means for delivering the IUD with the retrieval thread into the uterus. Generally, in the embodiments described herein, the—cut retrieval thread is not used to perform the loading and securement functions of IUD placement, as with prior art devices, and therefore, the retrieval thread may be made short enough at the time of manufacture such that it does not require cutting after IUD delivery into the uterus.

Figure 1A:
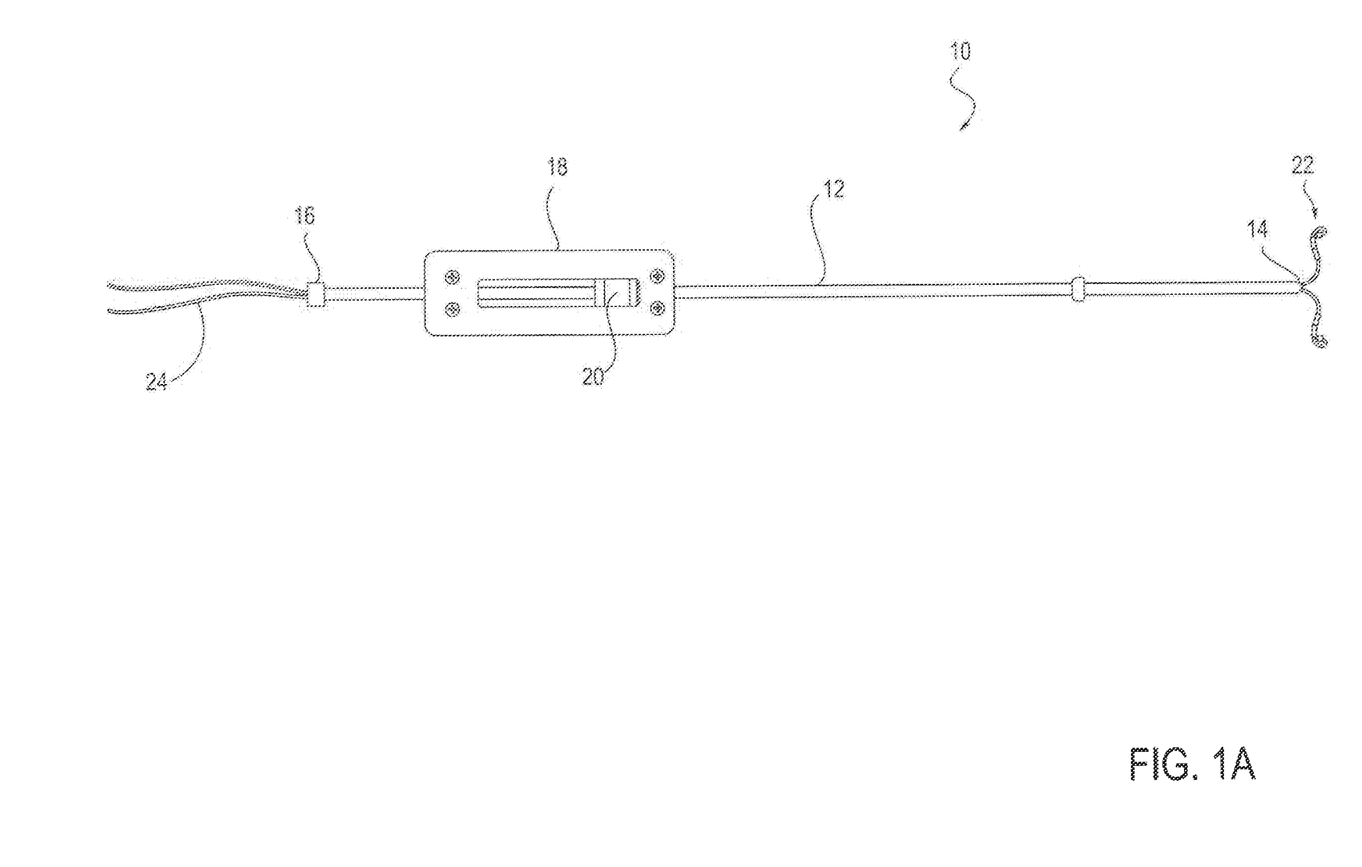
FIG. 1A illustrates an IUD and inserter system, according to one embodiment.
Figure 1B:
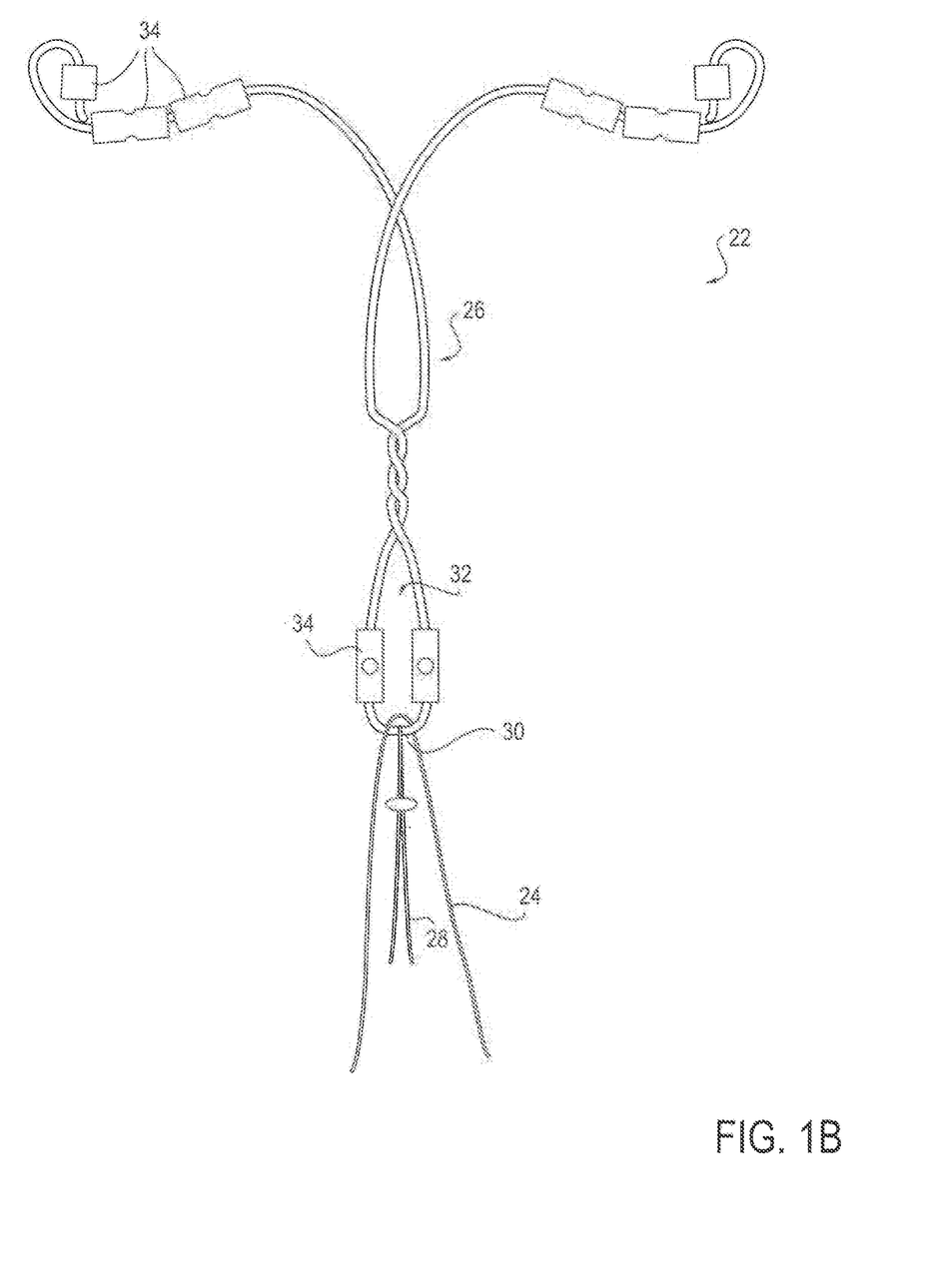
FIG. 1B illustrates the IUD of FIG. 1A in close-up.

Referring to FIG. 1A, in one embodiment, an IUD system 10 may include an IUD 22 and an inserter 12 (or "inserter device" or "insertion device"). The inserter 12 may include a distal end 14 (into which the IUD 22 is loaded), a proximal end 16, and a handle 18 with a slider 20. Referring to FIG. 1B, the IUD 22 may include a frame 26, a retrieval thread 28, and a release thread 24. In some embodiments, the frame 26 may include an opening 32 at or near a midpoint 30 along the length of the frame 26. This midpoint 30 may also be referred to as the "distal end" of the IUD 22, or in other words the end of the IUD 22 that is closest to the cervix when the IUD 22 is delivered to the uterus. The retrieval thread 28 is permanently attached to the frame 26, in some embodiments at or near the midpoint 30 and/or the opening 32. The release thread 24 may pass through the opening 32. Also attached to this embodiment of the IUD are multiple copper sleeves 34. Alternatively, however, the IUD 22 may be a hormonal IUD, have different copper-carrying members, be a hormone/copper combination device, or not include copper or hormone. In other words, the two-string configuration described herein may be applied to any type of IUD, according to various alternative embodiments.

As just mentioned, the IUD 22 includes a two-thread IUD insertion system that allows for the secure delivery of the IUD 22 into the uterus, with an integral retrieval thread 28 that has a predetermined length that does not require cutting after delivery of the IUD. The release thread 24 is configured to secure the IUD 22 in the distal end 14 of the inserter 12. Thus, the release thread 24 holds the IUD 22 within the inserter 12 until the IUD 22 is released. In some embodiments, referring again to Figure IA, the release thread 24 extends from a first end, located outside the proximal end 16 of the inserter 12, through the shaft of the inserter 12, through the IUD 22, and back out of the proximal end 16. By attaching to the proximal end 16 of the inserter 12 and releasably attaching to the IUD 22, the release thread 24 may be used to hold onto the IUD 22 as it is unsheathed from the inserter 12, fully opens to its default, expanded shape, and is positioned and possibly repositioned within the uterus, all before being released for final placement. The release thread 24 is releasably coupled with the IUD 22 (not permanently attached), so when it is no longer needed for securing the IUD 22 to the inserter 12, the release thread 24 may simply be pulled off the IUD 22.

The retrieval thread 28 is permanently attached to the frame 26 of the IUD 22 at an attachment point and has a predetermined length (measured from the attachment point with the frame 26 to the ends of the retrieval thread 28) in a range of about 5 cm to about 9 cm, and more ideally about 5.5 cm to about 8.8 cm, and even more ideally about 7 cm to about 8 cm. In one specific embodiment, the retrieval thread may have a length of about 7.8 cm. The predetermined length is selected such that, in the vast majority of patients, the resulting exposed length in the vaginal cavity will be approximately 3-4 cm from the external os of the cervix, as is clinically desirable. With this configuration, the physician will typically not be required to cut the retrieval thread 28, thereby eliminating a deployment step, saving valuable time, and reducing the use of instrument resources. The IUD delivery system 10 also reduces risk of injury and infection to the patient, as the physician does not need to advance a sharp object or instrument into the vaginal cavity after IUD deployment for cutting. Additionally, there is less risk of inadvertent IUD dislodgement and/or removal, which may occur using currently available systems when the scissors do not completely cut the thread and accidentally grasp it and pull on it.

Although the retrieval thread 28 is illustrated in FIG. 1B (and FIG. 2E) as having two strings extending from the IUD 22, alternative embodiments may have only one string or may have more than two strings. In one alternative embodiment, for example, one end of a retrieval thread may be attached to the IUD 22, and an opposite end may be a free end, such that retrieval thread includes only one "string." In alternative embodiments, a retrieval thread may include three or more "strings."

Both the retrieval thread 28 and the release thread 24 may be made of any suitable material, such as but not limited to any monofilament or other suture material currently available or as yet to be invented, or any other biocompatible material that may be used to make a thread or string. Various embodiments may be coated or uncoated.

In various embodiments, the retrieval thread 28 may also include a colored marker, multiple colored markers, or one or more color changes along the length of the thread 28. For example, a marker may be placed on the retrieval thread 28 between about 1 cm and about 3 cm (ideally about 2 cm) from an attachment point of the thread 28 to the IUD 22. The marker, markers or color change on the retrieval thread 28 will provide sufficient contrast such that a physician will be able to view the marker/color change inside the vaginal cavity after placement of the IUD 22. Since the marker or color change is a known distance from the attachment point with the IUD 22, the physician will be able to determine if the IUD 22 is placed too low within the uterus, or at later patient visits, determine that the ID has moved from its originally placed position. In some embodiments, the physician may view one or more markers inside the vaginal cavity to make the determination. In other embodiments, the physician may view the retrieval thread 28 and not see a marker, and this inability to view the marker may confirm correct placement. At later patient visits, the physician may again view the marker or color change to determine if the IUD 22 has displaced inferiorly over time. In various embodiments, the marker(s) and/or color change(s) on the retrieval thread 28 may be viewed by the naked eye or by a scope or other viewing device.

The retrieval thread 28 may include markers and/or color changes that have any suitable color combinations, as long as the color combinations provide sufficient contrast to make the change visible to a physician. In one embodiment, for example, a first portion of the retrieval thread 28 closest to the IUD 22 may be white, and a second portion at the end of the retrieval thread 28 may be blue. Typically, the marker will be simply a change in color of the retrieval thread 28, rather than an additional piece or suture, to reduce the risk of debris accumulation and/or infection. Since the length of an average cervix is about 3 cm, positioning the marker less than about 3 cm away from the attachment of the retrieval thread 28 to the IUD 22 is preferable in at least some embodiments. Visualization of the marker in the vagina will indicate that the bottom of the device is within the cervix, which is considered too low for optimal clinical efficacy. In the embodiment in which the first portion of the retrieval thread 28 is blue and the second portion is white, for example, the physician may view the thread 28 in the vaginal cavity. If only the second, blue portion of the retrieval thread 28 is showing (the end of the thread, in this example), the physician may confirm that the IUD 22 is placed sufficiently high in the uterus. If the first, white portion and part of the blue portion of the retrieval thread 28 are showing (the white portion being the portion closest to the IUD 22, in this example), then the physician may determine that the IUD 22 is positioned too low in the uterus.

Low position of an IUD within a uterus is a significant cause of IUD failure and subsequent pregnancies. Physicians have no currently available, reliable way to identify a low position, other than using an imaging modality, such as ultrasound or x-ray fluoroscopy. Ultrasound is expensive and typically not readily available in family planning clinics, especially in developing countries. Fluroscopy is even more expensive, complicated and time-consuming. Including a marker on the retrieval thread 28 will allow a physician to identify low position easily during routine examination of the cervix performed in the gynecologist office.

With reference now to FIGS. 2A-2E, one embodiment of a method for using the IUD system 10 described in relation to FIGS. 1A and 1B will now be described. In various alternative embodiments, one or more of the steps described here may be altered or skipped, and/or the order of the steps may be changed, without departing from the scope of the invention. Therefore, the following description should not be interpreted as limiting the method as it is described in the claims.

Figure 2A:
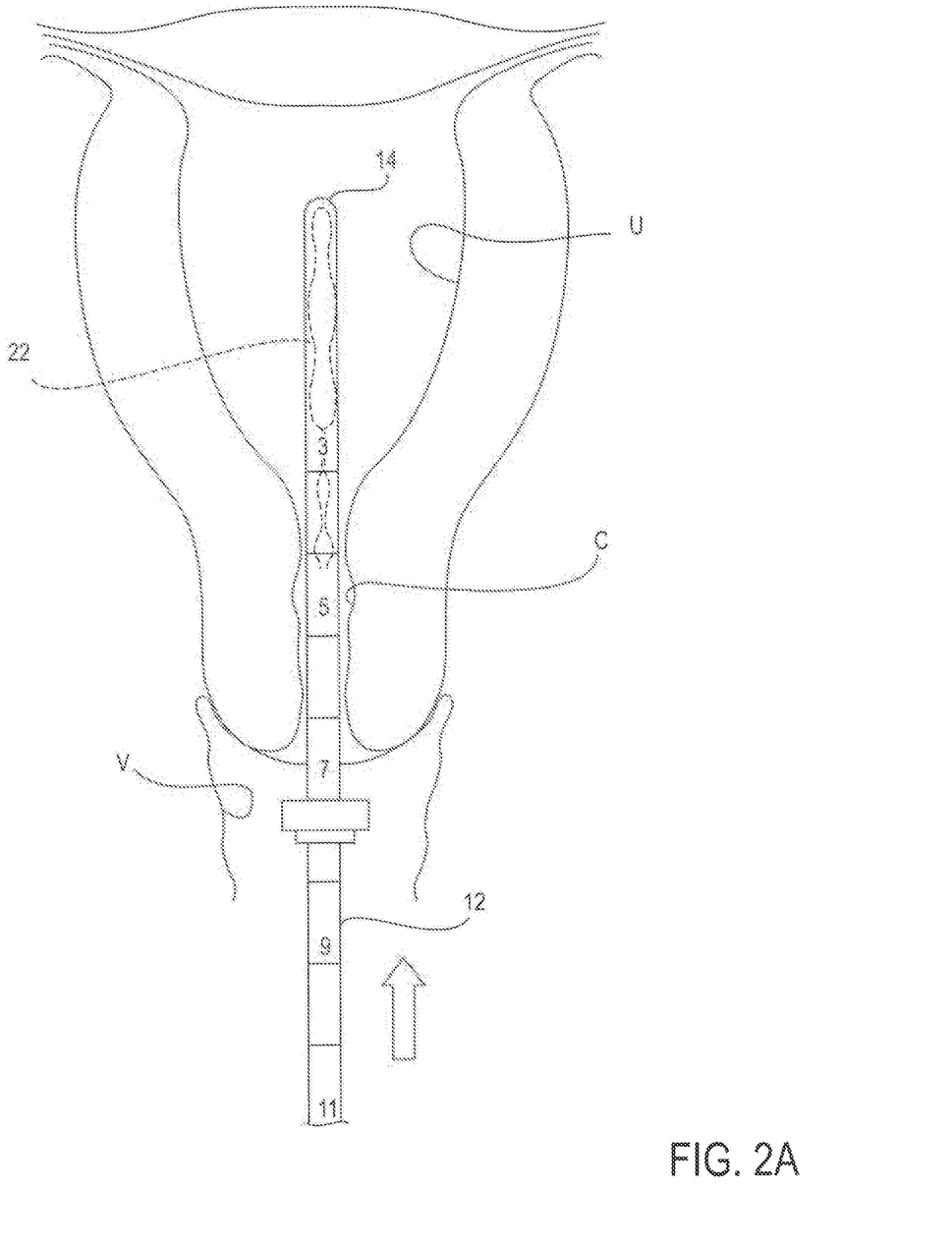
FIGS. 2A-2E illustrate a method for inserting an IUD, using an IUD inserter device, according to one embodiment.

As illustrated in FIG. 2A, a first step of an IUD insertion method may involve advancing the inserter 12 through the vaginal cavity V and the cervix C to position the distal end 14 of the inserter 12 in the uterus U. During advancement of the distal end 14 into the uterus U, the IUD 22 is typically housed completely, or mostly, within the inserter 12. In alternative embodiments, however, a portion, or all, of the IUD 22 may protrude out of the distal end 14 during advancement.

Figure 2B:
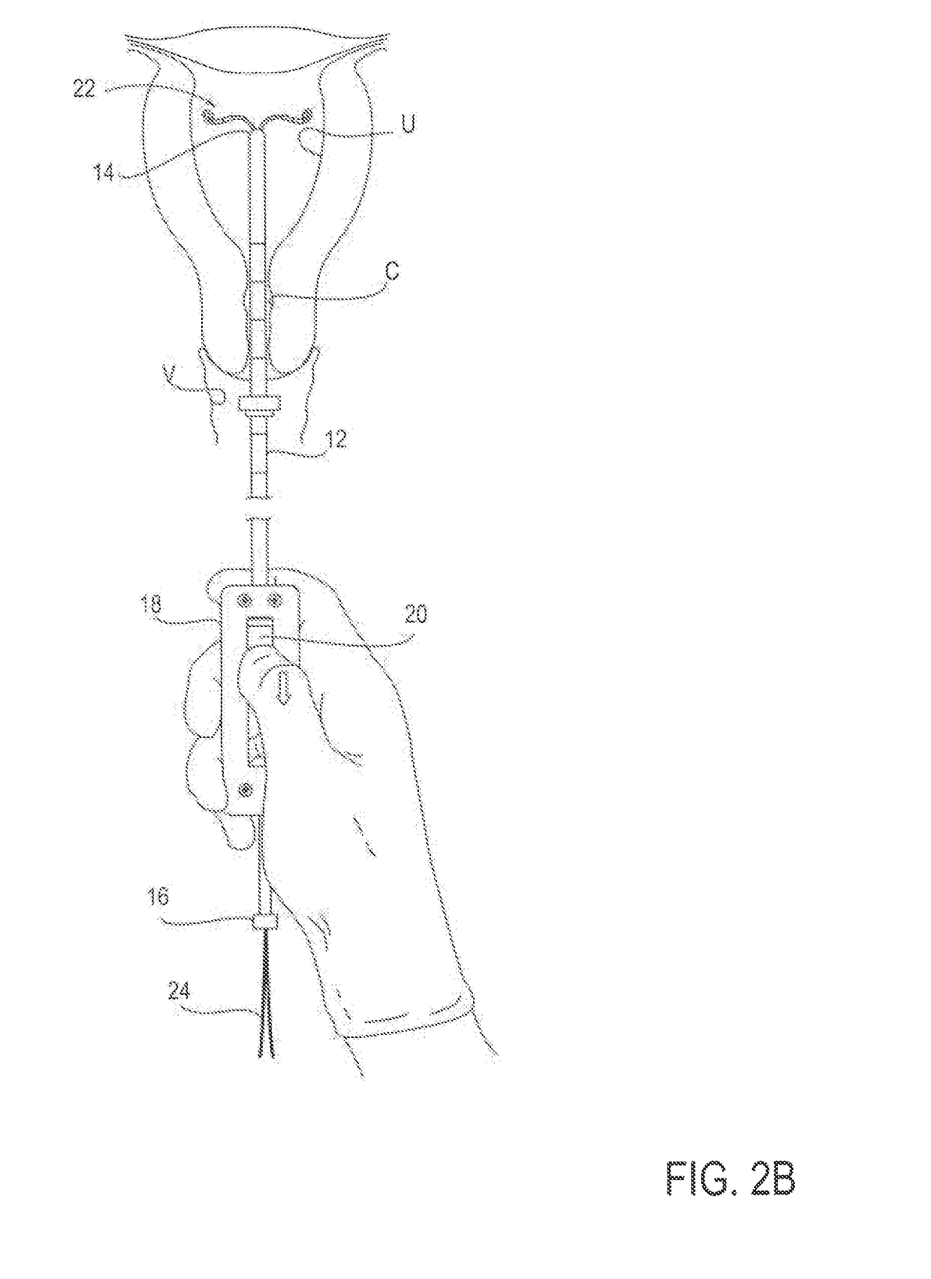

Referring to FIG. 2B, a next step may involve sliding the slider 20 of the inserter 12 proximally (solid arrow on figure), relative to the handle 18, to cause the IUD 22 to advance out of the distal end 14 of the inserter 12 by uncovering the IUD 22. In alternative embodiments, the inserter 12 may include other mechanisms for advancing the IUD 22 out of the distal end 14, such as by advancing the slider 20 when it attached to a movable inner member, thereby pushing the IUD 22 out of the inserter 12. During this phase of the method, the IUD 22 does not touch the top (or "fundus") of the uterus U.

Figure 2C:
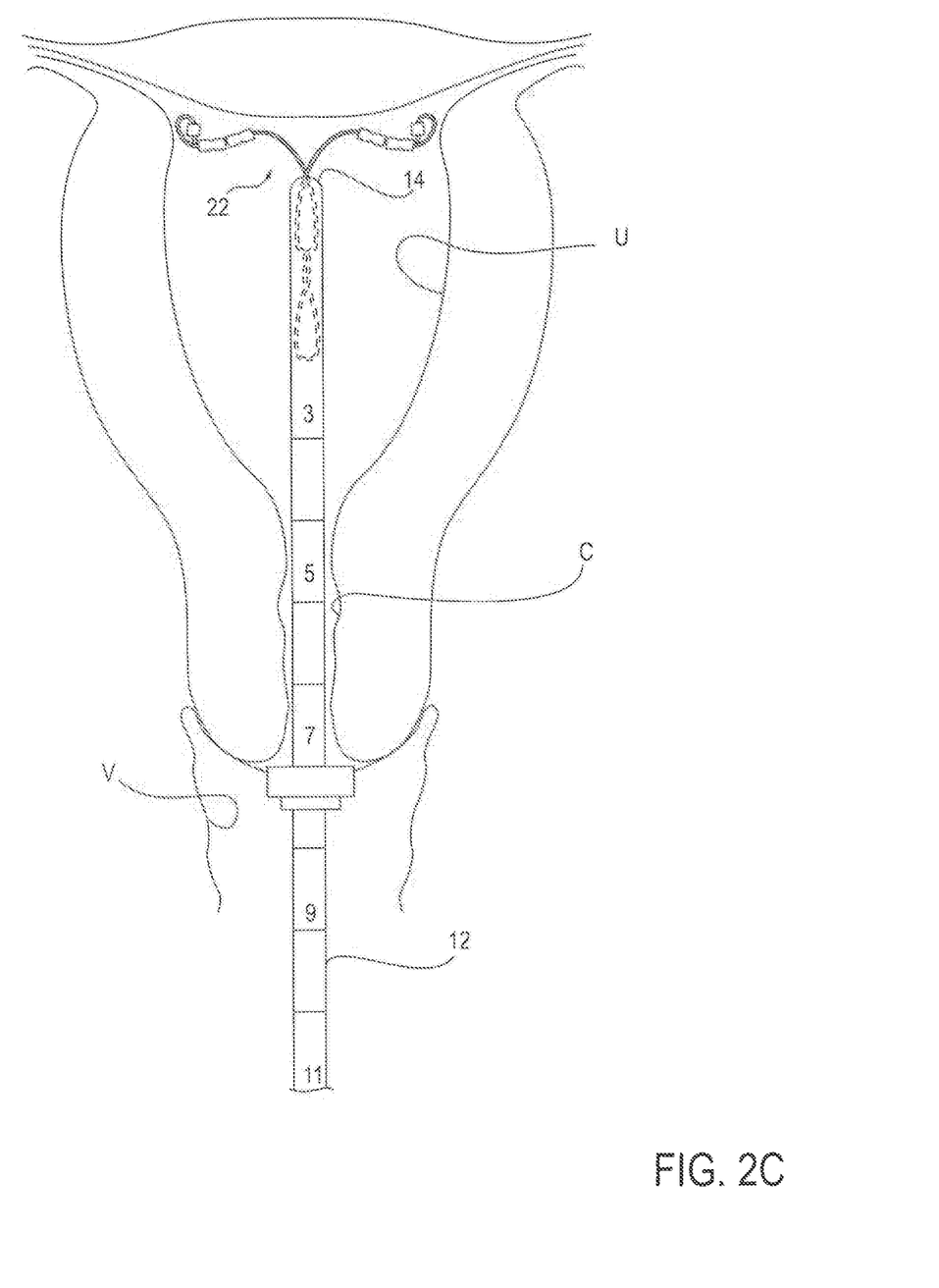

FIG. 2C illustrates an optional step of advancing the inserter 12 farther into the uterus U to contact the IUD 22 with the fundus of the uterus U. This step is optional, because the IUD 22 may alternatively be released lower in the uterus U and allowed to move up the uterus U as it expands.

Figure 2D:
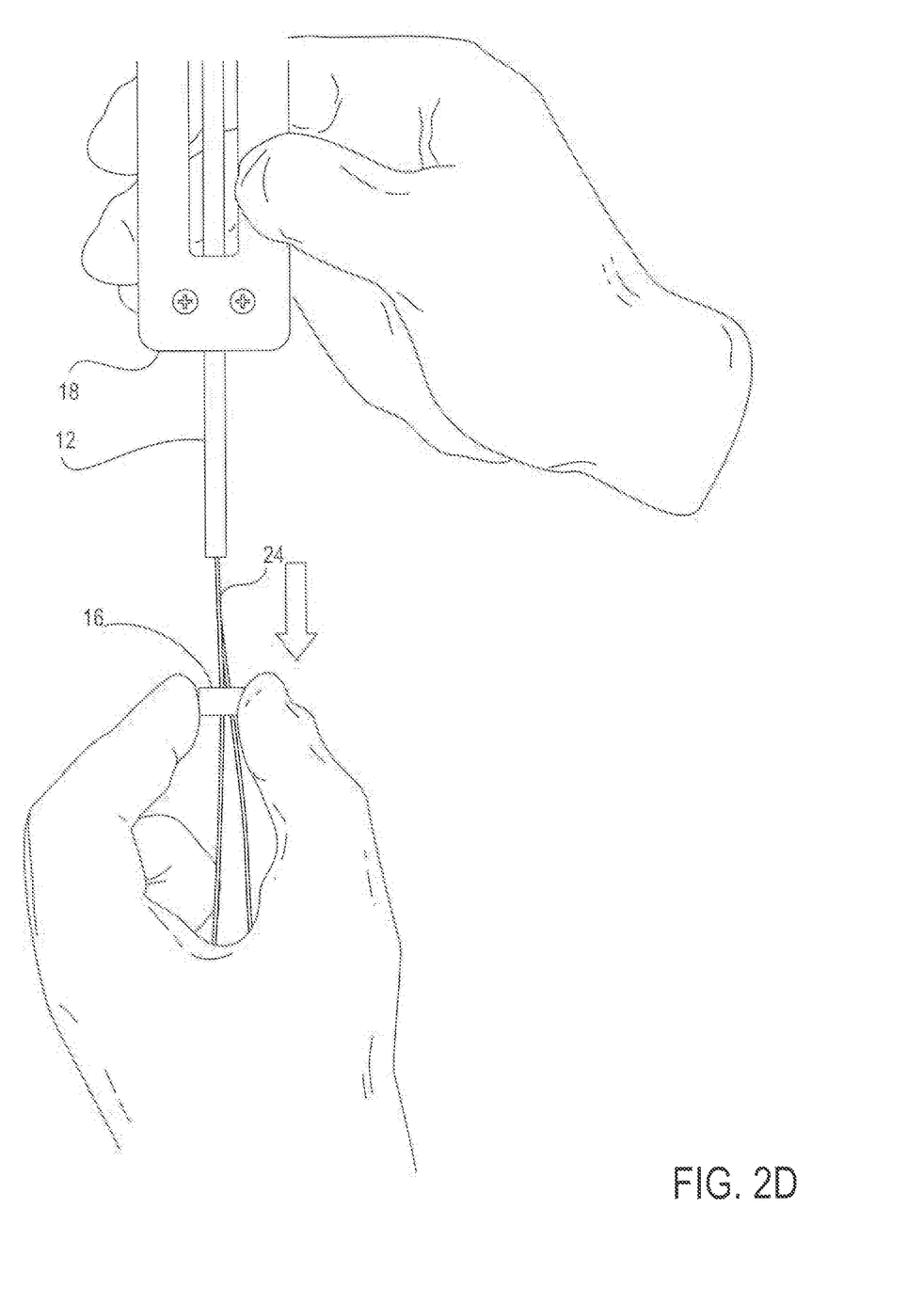

With reference to FIG. 2D, the method may next involve removing the proximal end 16, which in this embodiment is a cap, from the inserter 12. This proximal end 16 cap, while it is attached to the inserter 12, serves to hold and lock onto the release thread 24 to the inserter 12. When the proximal end 16 cap is removed, the release thread 24 is free to be pulled off of the IUD 22. In various alternative embodiments, any suitable locking mechanism may be used for holding and then releasing the release thread 24 at the proximal end 16 of the inserter 12.

Figure 2E:
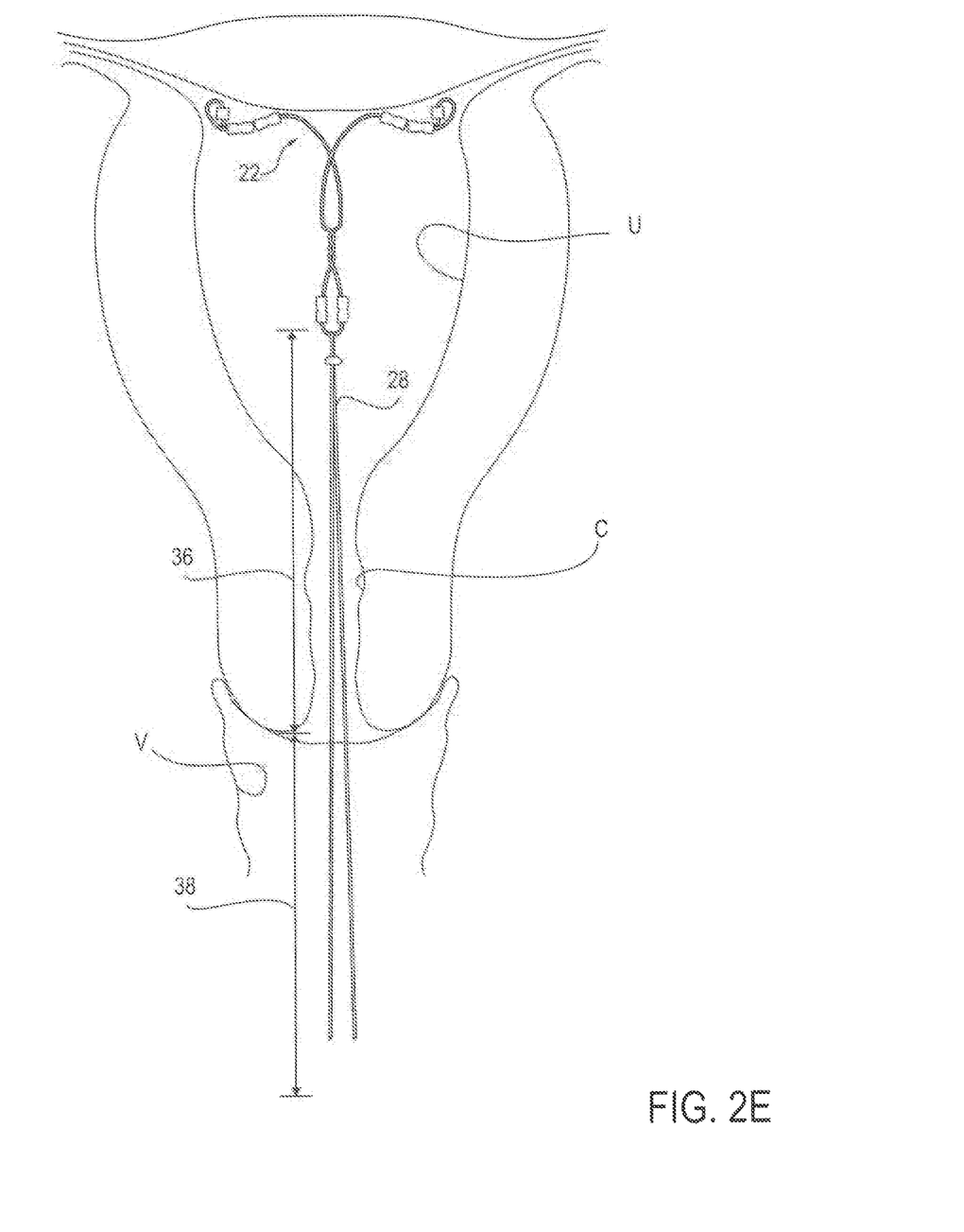

Finally, referring to FIG. 2E, once the release thread 24 is released from its attachment to the proximal end 16 of the inserter 12, so that it can be pulled off of the IUD 22, the release thread 24 and the inserter 12 may be removed from the patient. In various embodiments, this removal step may be accomplished by pulling the inserter 12 and release thread 24 out together, or alternatively by pulling out one first and then the other. After the inserter 12 and removal thread 24 are removed, the IUD 22 remains in the uterus U, with the retrieval thread 28 extending through the cervix C into the vaginal cavity V. Typically, the retrieval thread 28 will not need to be cut or shortened in any way. In this embodiment, the retrieval thread 28 includes a first portion, having a first length 36 and a first color, and a second portion, having a second length 38 and a second color. As described above, the overall length of the retrieval thread 28 will typically be between about 5 cm and about 9 cm, as measured from the attachment point to the ends of the two strings (length 36 plus length 38). The first length 36 will typically be about 3 cm or less, and may be about 2 cm or less. The second length may be between about 3 cm and about 4 cm in some embodiments. As mentioned above, in alternative embodiments, the retrieval thread 28 may include one string or three or more strings, rather than two strings, as pictured in in FIG. 2E. In one embodiment, the first portion of the retrieval thread 28 may be white, and the second portion may be blue, although any alternative color combination or marker combination may alternatively be used. Once the IUD 22 is delivered, the physician may view the retrieval string 28 in the vaginal cavity. If only blue thread is visible, the physician may conclude that the IUD is sufficiently far into the uterus U. If white thread is visible, the physician may conclude that the IUD is too low in the uterus U.

Although various embodiments and features are described herein, the present invention extends beyond the specifically disclosed embodiments to other alternative embodiments and/or uses of the invention and obvious modifications and equivalents thereof. Thus, the scope of the present invention herein disclosed should not be limited by the particular disclosed embodiments described above.

What is claimed is:

1. An intrauterine contraceptive system comprising:
   an insertion device comprising a distal end configured to contain an intrauterine contraceptive device, wherein the insertion device is configured to release the intrauterine contraceptive device into a uterus when the insertion device is inserted into the uterus;
   an intrauterine contraceptive device, wherein the intrauterine contraceptive device is in a delivery configuration when contained within the distal end of the insertion device and wherein the intrauterine contraceptive device is configured to expand to a deployable configuration after being deployed from the distal end of the insertion device;
   a retrieval thread permanently attached to the intrauterine contraceptive device;
   a release thread releasably coupled to the intrauterine contraceptive device and configured to secure the intrauterine contraceptive device to the distal end of the insertion device, wherein the release thread is configured to be pulled off the intrauterine contraceptive device to release the intrauterine contraceptive device from the insertion device.

2. The intrauterine contraceptive system of claim 1, wherein the retrieval thread does not require cutting after the intrauterine contraceptive device is released into a uterus.

3. The intrauterine contraceptive system of claim 2, wherein the retrieval thread has a length between 5 cm and 9 cm.

4. The intrauterine contraceptive system of claim 1, wherein the insertion device further comprises a proximal end configured to be coupled to the release thread.

5. The intrauterine contraceptive system of claim 4, wherein the proximal end comprises a cap configured to be coupled to the release thread.

6. The intrauterine contraceptive system of claim 1, wherein the intrauterine contraceptive device comprises an opening through which the release thread passes.

7. The intrauterine contraceptive system of claim 6, wherein the insertion device comprises a proximal end comprising a cap configured to be coupled to the release thread.

8. The intrauterine contraceptive system of claim 7, wherein the cap is configured to be removed from the proximal end of the insertion device and pulled to pull the release thread off the intrauterine contraceptive device.

9. The intrauterine contraceptive system of claim 1, wherein the intrauterine contraceptive device comprises a wire frame comprising a distal end, two arms extending laterally, and one or more substance delivery members.

10. The intrauterine contraceptive system of claim 9, wherein the distal end of the intrauterine contraceptive device comprises an opening through which the release thread passes.

11. The intrauterine contraceptive system of claim 10, wherein the one or more substance delivery members are copper sleeves, copper wires, hormone delivery sleeves, drug delivery depots, drug coatings, or drug eluting carriers.

\* \* \* \* \*